United States Patent
Yokoyama et al.

(10) Patent No.: US 6,998,465 B2
(45) Date of Patent: Feb. 14, 2006

(54) PROCESS FOR PRODUCING BORIC ESTER COMPOUND, ELECTROLYTE FOR ELECTROCHEMICAL DEVICE, AND SECONDARY BATTERY

(75) Inventors: Shoichi Yokoyama, Kanagawa (JP); Takeshi Yabe, Kanagawa (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 10/489,418

(22) PCT Filed: Sep. 27, 2002

(86) PCT No.: PCT/JP02/10049

§ 371 (c)(1), (2), (4) Date: Mar. 12, 2004

(87) PCT Pub. No.: WO03/031453

PCT Pub. Date: Apr. 17, 2003

(65) Prior Publication Data

US 2004/0266981 A1    Dec. 30, 2004

(30) Foreign Application Priority Data

Sep. 28, 2001 (JP) .............................. 2001-301122
Mar. 29, 2002 (JP) .............................. 2002-098060

(51) Int. Cl.
*C08G 79/58* (2006.01)
(52) U.S. Cl. ...................... 528/394; 528/425; 528/495; 528/501
(58) Field of Classification Search ................ 528/394, 528/425, 495, 561; 429/126
See application file for complete search history.

(56) References Cited

FOREIGN PATENT DOCUMENTS

| | | |
|---|---|---|
| EP | 1 160 268 | 12/2001 |
| EP | 1 258 938 | 11/2002 |
| JP | 47-29323 | 11/1972 |
| JP | 2001-72875 | 3/2001 |
| JP | 2001-72876 | 3/2001 |
| JP | 2001-72877 | 3/2001 |
| JP | 2001-273925 | 5/2001 |
| JP | 2001-155771 | 6/2001 |
| JP | 2002-158039 | 5/2002 |
| JP | 2002-348323 | 12/2002 |
| WO | WO 01/18094 | 3/2001 |
| WO | WO 01/39316 | 5/2001 |

OTHER PUBLICATIONS

International Search Report mailed Feb. 4, 2003, for No. PCT/JP02/10049.

*Primary Examiner*—Duc Truong
(74) *Attorney, Agent, or Firm*—Antonelli, Terry, Stout and Kraus, LLP.

(57) ABSTRACT

A process for producing a boric acid ester compound which comprises esterifying a compound represented by the formula (1):

$$X-[O(AO)_n-H]_a \qquad (1)$$

wherein X represents a group independently selected from a residue of a compound having 1 to 6 hydroxyl groups, an acryloyl group and a methacryloyl group with a boron-containing compound represented by the formula (2):

$$(RO)_3-B \qquad (2)$$

wherein R represents an alkyl group having 1 to 4 carbon atoms. The present invention can provide a boric acid ester compound which has a high ion conductivity, which is useful as a material for an electrochemical device, such as a secondary battery or a capacitor, having excellent safety and which is low in water and impurity contents, a polymer electrolyte containing the boric acid ester compound, and a secondary battery using the polymer electrolyte.

15 Claims, No Drawings

PROCESS FOR PRODUCING BORIC ESTER COMPOUND, ELECTROLYTE FOR ELECTROCHEMICAL DEVICE, AND SECONDARY BATTERY

TECHNICAL FIELD

The present invention relates to a process for producing a boric acid ester compound of the compound having an oxyalkylene group, to an electrolyte for an electrochemical device using the boric acid ester compound or a polymer thereof, and to a secondary battery.

BACKGROUND ART

In recent years, there is a strong demand for high performance and compact electronic devices. Thus, battery materials such as a lithium ion secondary battery, which are an energy source for such devices, are also required to be compact and light weight and to have a high capacity and a high energy density. As a consequence, there have been made various studies and developments on batteries. In general, a lithium ion secondary battery has a construction having a positive pole comprising a metal oxide, a negative pole comprising a carbonaceous material, and a separator and an electrolyte liquid sandwiched between both the poles. Such a second battery having a high energy density is actually used but is now desired to be further improved.

To cope with this demand, an attempt has been made to apply a solid electrolyte, which is a new ion conductor to be substituted for the conventional electrolyte solution, to electrochemical devices such as totally solid primary batteries, secondary batteries, and capacitors. Thus, various polymer electrolytes using a polymer compound as an electrolyte are now being studied. Polymer electrolytes have features that they have a flexibility and can follow mechanical shocks and volume changes of the electrodes that occur as a result of ion-electron exchange reaction between the electrodes and the electrolyte. As such a polymer electrolyte, U.S. Pat. No. 4,303,748 proposes a solid electrolyte comprising a polyalkylene oxide in which an alkali metal salt or an alkaline earth metal salt is dissolved. This electrolyte has a problem that the working efficiency is poor because a long time is required to dissolve the above salt. Further, the electrolyte has problems that its ion conductivity is not sufficient and its contact resistance with the electrodes is high. Such an insufficient ion conductivity and a high contact resistance result in an insufficient current density during charging and discharging so that the electrolyte may be used only for limited applications and cannot be used for applications requiring a large current.

To overcome the defects of the above solid electrolyte, there have been proposed a multitude of solid electrolytes including an alkali metal salt or an alkaline earth metal salt dissolved in a polymer having a poly(meth)acrylate main chain into which polyalkylene glycol chains are introduced as side chains and/or crosslinking chains. As one example of such polymer electrodes, JP-B-Hei3-73081 discloses a solid electrolyte having an alkali metal salt or an alkaline earth metal salt dissolved in an acryloyl-modified polyalkylene oxide. This electrode still has problems that its ion conductivity is insufficient, and further, the mobility of cation components affecting the charging and discharging is low. Such an insufficient ion conductivity and a low cation component mobility result in limitation of usage of the electrode, as mentioned above. Further, there is caused an additional problem that the electrode deteriorates in charging and discharging cycles because undesirable side reactions occur by movement of the counter anion.

For the purpose of controlling movement of ions affecting charging and discharging in a polymer electrolyte containing as a main ingredient a ring-open polymerization product from an alkylene oxide derivative, JP-A-Hei11-54151 and JP-A-2001-55441 propose an electrolyte using a trifunctional boron compound such as a boroxin ring capable of capturing counter anion of the metal salt. As the boron-containing compound for use in obtaining these compounds, orthoboric acid or boron oxide is used. In this case, however, water is produced during the reaction. Further, the above compound thus obtained is easily hydrolyzed with water. Therefore, it is very difficult to remove the water produced by the reaction. For this reason, residual water in the compound thus obtained is unavoidable, which may cause troubles when used as an electrolyte substrate. JP-A-2001-72876 and JP-A-2001-72877 propose an electrolyte of a boron-containing compound and refer to borane as a base material for obtaining the compound. Borane, however, has very strong activity and exhibits spontaneous combustibility in the air so that it is difficult to handle borane for production of the boron-containing compound. Additionally, when borane is used for reaction with a polymerizable group-containing compound, there is a possibility that the polymerizable group is damaged thereby.

On the other hand, there has been a proposal to use a polymeric boric acid ester as an electrolyte. It is known that a boric acid ester compound is obtainable by reaction of an alcohol with boric acid or anhydrous boric acid. Namely, the reaction in the case of using an alcohol and boric acid is as shown in the formula [1] below, while the reaction in the case of using an alcohol and anhydrous boric acid is as shown in the formula [2] below:

$$H_3BO_3 + 3ROH \rightarrow B(OR)_3 + 3H_2O \qquad [1]$$

$$B_2O_3 + 3ROH \rightarrow B(OR)_3 + H_3BO_3 \qquad [2]$$

Since the boric acid ester compound has extremely high hydrolyzable property, it produces boric acid and an alcohol upon contact with water according to the reverse reaction of the formula [1]. In fact, the reaction of the formula [1] is an equilibrium reaction. The equilibrium is, however, extremely partial to the left, i.e. toward the direction resulting in the hydrolysis of the boric acid ester and the formation of boric acid and alcohol. Therefore, with the normal operation, the yield of the boric acid ester is extremely low. In this circumstance, it is a general practice, in the reaction of an alcohol and boric acid, to use an azeotropic dehydrating agent such as benzene to successively remove water produced in situ by the reaction from the reaction liquid, so as to shift the equilibrium of the above formula rightward and to recover the end product. Even with this method, because the equilibrium of the formula [1] is extremely partial to the left, the dehydration efficiency becomes poor as the reactivity increases and, therefore, there is a limitation on reduction of the water content. In addition, there is a problem that it is necessary to reduce the contents of boric acid and alcohol in order to obtain a high purity boric acid ester.

That is, while the use of an alcohol in an excessive amount is advantageous from the standpoint of an increase in the reaction rate and dehydration efficiency, it is difficult to evaporate the alcohol when the alcohol has a high molecular weight or when the alcohol has a polymerizable group which is susceptible to undergo polymerization upon heating. Thus, the alcohol is apt to remain unremoved in the system.

When such a compound having a hydroxyl group remains in the system, the performance of an electrochemical device is markedly deteriorated, though depending upon its use.

When boric acid is used in an excessive amount, there is obtained a mixture of the boric acid ester and boric acid. When this mixture is heated, the boric acid ester is decomposed so that the yield is reduced. To cope with this problem, JP-A-Hei3-74390 discloses a method in which boric oxide and -an aliphatic alcohol are reacted to obtain a reaction liquid containing a boric acid ester and boric acid, the boric acid is then separated by filtration from the reaction liquid and the filtrate is distilled. This publication indicates that, if distilled without the separation of boric acid by filtration, the decomposition of boric acid ester and boric acid is accelerated as described above, thereby lowering the yield of the end product. This method, however, is applicable only to the production of compounds such as boric acid ester compounds of aliphatic alcohols which permit the separation of boric acid by filtration and which permit the purification by distillation.

In contrast, with the method using anhydrous boric acid as shown in the formula [2], 50% of the boron supplied may be converted into a boric acid ester without using an azeotropic dehydrating agent. However, the remainder of the boric acid is esterified through the reaction similar to the formula [1]. Therefore, there still remains a limitation on obtaining a high purity boric acid ester as described above.

Thus, when such a boric acid ester containing a large amount of impurities is used as a raw material for an electrolyte, there is a problem of high possibility of causing deterioration of electrolyte characteristics such as an increase in resistance of solid electrolyte interface (SEI), a reduction of charging-discharging cycle performance, and a reduction of potential stability. In particular, as far as an electrolyte for lithium ion secondary batteries is concerned, there is a great tendency that impurities contained in the boric acid ester compound will react with lithium to generate a gas, thereby causing a problem of reduction of the safety of the batteries.

In this circumstance, there is a demand for high purity boric acid ester compounds which contain a reduced amount of impurities such as water and which are usable as an electrolyte for electrochemical devices, etc.

DISCLOSURE OF THE INVENTION

It is an object of the present invention to provide a process for producing a boric acid ester compound which has a high ion conductivity, which is useful as a material for an electrochemical device, such as a secondary battery or a capacitor, having excellent safety, and which is low in water content and impurity content, to provide a polymer electrolyte containing the boric acid ester compound and to provide a secondary battery using the polymer electrolyte.

Thus, the present invention provides the following:

(A) A process for producing a boric acid ester compound which comprises esterifying a compound represented by the formula (1):

$$X—[O(AO)_n—H]_a \quad (1)$$

wherein X represents a group selected from a residue of a compound having 1 to 6 hydroxyl groups, an acryloyl group and a methacryloyl group, AO represents an oxyalkylene group having 2 to 4 carbon atoms, n is 0 to 600, a is 1 to 6, and n×a is 0 to 600, with a boron-containing compound represented by the formula (2):

$$(RO)_3—B \quad (2)$$

wherein R represents an alkyl group having 1 to 4 carbon atoms;

(B) The process for producing a boric acid ester compound as recited in (A), wherein the compound represented by the formula (1) has an average molecular weight of 110 or more;

(C) The process for producing a boric acid ester compound as recited in (A) or (B) which comprises reacting the compound represented by the formula (1) with the boron-containing compound represented by the formula (2), while distilling the boron-containing compound represented by the formula (2) and an alcohol represented by the formula (3) and produced by said reaction:

$$ROH \quad (3)$$

wherein R represents an alkyl group having 1 to 4 carbon atoms;

(D) The process for producing a boric acid ester compound as recited in any one of (A) to (C), wherein the boron-containing compound represented by the formula (2) is used in an amount of ⅓ mole or more per 1 mole of the hydroxyl group of the compound represented by the formula (1);

(E) The process for producing a boric acid ester compound as recited in any one of (A) to (D), wherein the boric acid ester compound has a water content of 1,000 ppm or less when measured by Karl Fischer titration;

(F) An electrolyte for an electrochemical device, which comprises a boric acid ester compound obtainable by the process recited in any one of (A) to (E) or a polymer thereof;

(G) A secondary battery using the electrolyte for an electrochemical device as recited in (F); and (H) An electrolyte for an electrochemical device, which has water content of 1,000 ppm or less when measured by Karl Fischer titration and which comprises a boric acid ester compound represented by the formula (4) or a polymer thereof:

$$B—[O(AO)_p—Y]_3 \quad (4)$$

wherein Y represents a group selected from an acryloyl group, a methacryloyl group and an alkyl group having 1 to 4 carbon atoms with the proviso that at least one of Y groups is an acryloyl group or a methacryloyl group, AO is an oxyalkylene group having 2 to 4 carbon atoms, and p is 1 to 600.

BEST MODE FOR CARRYING OUT THE INVENTION

The present invention will be described below in further detail.

In the compound represented by the formula (1) used in the production method of the present invention, X represents a group selected from a residue of a compound having 1 to 6 hydroxyl groups, an acryloyl group, and a methacryloyl group. The residue of a compound having hydroxyl groups as used herein is intended to refer to a group obtained by removing a hydroxyl group from such a compound.

As the oxyalkylene group having 2 to 4 carbon atoms which is represented by AO in the formula (1), there may be mentioned, for example, an oxyethylene group, an oxypropylene group, an oxybutylene group, and an oxytetramethylene group. An oxyethylene group or oxypropylene group is preferred. These groups may be used singly or in combination of two or more. When there are two or more groups, the polymerization mode may be a block type or a random type.

The symbol "n" represents an average number of mols of the added oxyalkylene groups having 2 to 4 carbon atoms and is 0 to 600, preferably 1 to 200, more preferably 1 to 100, for reasons of suitable ion conductivity. When n exceeds 600, the amount of boron introduced is so small that it is difficult to provide a suitable anion capturing property when the compound is used as an electrolyte.

The symbol "a" is 1 to 6, preferably 1 to 4, particularly preferably 1. In this case, n×a is 0 to 600, preferably 1 to 400, more preferably 1 to 200. When n×a is greater than 600, the amount of the boric acid ester bonds introduced is so small that it is difficult to provide a suitable anion capturing property and, hence, to obtain a high ion conductivity.

The compound represented by the formula (1) serves as a substrate for the boric acid ester compound of the present invention and is obtainable by the ordinary ring-open polymerization. For example, the compound of the formula (1) may be synthesized by polymerizing an alkylene oxide having 2 to 4 carbon atoms, such as ethylene oxide, propylene oxide, butylene oxide or tetrahydrofuran, with a compound having 1 to 6 hydroxyl groups in the presence of a ring-open polymerization catalyst such as an alkali metal compound (e.g. sodium hydroxide, potassium hydroxide, lithium hydroxide or sodium methoxide) or a Lewis acid (e.g. a boron trifluoride etherate, tin tetrachloride or aluminum trichloride) at a predetermined molar ratio.

As the compound represented by X in the formula (1) and having 1 to 6 hydroxyl groups, there may be mentioned monools such as methyl alcohol, ethyl alcohol, propyl alcohol, isopropyl alcohol, n-butyl alcohol, 2-butyl alcohol, t-butyl alcohol, n-hexyl alcohol, n-octyl alcohol, isooctyl alcohol, decyl alcohol, dodecyl alcohol, tridecyl alcohol, tetradecyl alcohol, hexadecyl alcohol, octadecyl alcohol, octadecenyl alcohol, eicosyl alcohol, tetraeicosyl alcohol, allyl alcohol, methallyl alcohol, hydroxyethyl vinyl ether, 2-hydroxyethyl acrylate, 2-hydroxyethyl methacrylate, 2-hydroxypropyl acrylate, 2-hydroxypropyl methacrylate, 2-hydroxybutyl acrylate, 2-hydroxybutyl methacrylate, 4-hydroxybutyl acrylate, 4-hydroxybutyl methacrylate, glycerol 1,3-dimethacrylate, glycerol 1,3-diacrylate, glycerol 1-acrylate-3-methacrylate, trimethylolpropane dimethacrylate, phenol, 4-ethylphenol, methyl p-oxybenzoate, p-t-octylphenol, dodecylphenol, α-naphthol, β-naphthol, nonylphenol, phenylphenol, 4-phenoxyphenol, p-t-butylphenol, p-(methoxyethyl)phenol, 4-methoxyphenol, guaiacol, guetol, p-(α-cumyl)phenol, cresol, 4-cyano-4'-hydroxybiphenyl, xylenol, and n-heptyl paraben; diols such as ethylene glycol, propylene glycol, butanediol, pentanediol, hexanediol, octanediol, glycerol monomethacrylate, trimethylolpropane monomethacrylate, catechol, hydroquinone, 1,4-dihydroxynaphthalene, bisphenol A, hydrogenated bisphenol A, resolcinol, 4-t-butylcatechol, and 2-t-butylhydroquinone; triols such as glycerin, trimethylolpropane, pentaerythritol monomethacrylate, pentaerythritol monoacrylate, diglycerol monomethacrylate, diglycerol monoacrylate, and fluoroglycinol; tetraols such as pentaerythritol and diglycerin; pentaols such as triglycerin; and hexaols such as tetraglycerin and dipentaerythritol.

X is preferably a residue of methyl alcohol, ethylene glycol, propylene glycol, butylene glycol, 2-hydroxyethyl acrylate, 2-hydroxyethyl methacrylate, 2-hydroxypropyl acrylate, 2-hydroxypropyl methacrylate, glycerol monomethacrylate or glycerol monoacrylate, an acryloyl group, or a methacryloyl group.

In a production method of the present invention in which the distillation and reaction of a boron-containing compound and the reaction product are performed simultaneously, it is preferred that the compound represented by the formula (1) have an acryloyl group or a methacryloyl group, since the production can be performed with a reduced thermal load and the polymerizable groups are not impaired.

The number average molecular weight of the compound represented by the formula (1) is preferably 110 or more, more preferably 110 to 30,000. When the number average molecular weight is 110 or more, the compound represented by the formula (1) can sufficiently retain in the reaction liquid so that the reactivity can increase. Such a number average molecular weight is also preferable when the above-described distillation is carried out, because the distillate can be easily recovered and utilized.

The compound represented by the formula (1) may be used singly or in combination of two or more. When two or more compounds are used, it is preferred that the hydroxyl value of the mixture be not greater than 430.

It is preferred that the compound represented by the formula (1) be previously treated so as to reduce its water content. The water content is preferably 0.5% by weight or less. When the compound contains a large amount of water, boric acid produced by hydrolysis of the boric acid ester will remain in the system, so that, when it is used as an electrolyte for an electrochemical device, the performance of the device may be impaired.

As R of the boron-containing compound represented by the formula (2) used in the present invention, there may be mentioned a methyl group, an ethyl group, an n-propyl group, an isopropyl group, an n-butyl group, a 2-butyl group, an isobutyl group and a t-butyl group. For reasons of easiness in removal of the alcohol produced in the formation of a boric acid ester, the use of a methyl group, an ethyl group, an isopropyl group or a t-butyl group, particularly a methyl group, is preferable.

The boron-containing compound represented by the formula (2) may be used singly or in combination of two or more. For reasons of easiness in controlling the distillation and in recovery and purification of the raw material, the use of a single compound is more preferable.

In the production of a boric acid ester compound according to the present invention, the boron-containing compound represented by the formula (2) is added to the compound represented by the formula (1) and the mixture is subjected to boric acid ester exchange at 30 to 200° C. in a flow of an inert gas. Thereafter, an alcohol represented by the formula (3) produced by the interesterification is removed under atmospheric pressure or under a pressure from an inert gas atmosphere-pressurized condition to 0.013 kPa so that the interesterification further proceeds.

When the compound represented by the formula (1) does not have a (meth)acryloyl group ((meth)acryloyl is hereinafter intended to refer to acryloyl or methacryloyl), the reaction temperature is preferably 50 to 200° C., more preferably 60 to 150° C. In this case, it is preferred that a suitable amount of a nitrogen gas be streamed in the reaction vessel. When the reaction temperature is low, the interesterification of the boric acid ester does not proceed fast because the removal of the eliminated low molecular weight alcohol is insufficient. When the reaction temperature is higher than 200° C., the compound represented by the formula (1) is apt to be thermally deteriorated.

When the compound represented by the formula (1) has a (meth)acryloyl group, the reaction temperature is preferably 30 to 120° C., more preferably 60 to 90° C. In this case, it is preferred that a suitable amount of a dry air be streamed in the reaction vessel. When the reaction temperature is low, the interesterification of the boric acid ester does not proceed fast because the removal of the eliminated low molecular weight alcohol is insufficient. When the reaction temperature is higher than 200° C., there is a possibility to cause a difficulty in retaining the (meth)acryloyl group.

The reaction pressure may be suitably determined in view of the temperature, the kind of the boron-containing compound represented by the formula (2), etc., but is preferably in the range from an inert gas atmosphere-pressurized condition to 0.013 kPa. When the pressure is less than 0.013 kPa, it is difficult to sufficiently retain the boron-containing compound represented by the formula (2) in the reaction liquid. When the pressure is higher than the inert gas atmosphere-pressurized condition or atmospheric pressure, the temperature during the removal of the alcohol represented by the formula (3) is so high that there is a possibility of causing thermal deterioration of the compound. For reasons of improvement of purity of the boric acid ester compound of the present invention, it is preferred that the removal of volatile components be carried out finally at a reduced pressure of 0.013 to 6.67 kPa. The reaction conditions may be changed within the above-described ranges as the reaction proceeds.

The reaction time is 0.5 to 100 hours, preferably 2 to 50 hours. The reaction conditions and the apparatus may be so selected as to complete the reaction within the above time range. Too short a reaction time below 0.5 hour may cause a difficulty in removing a low molecular weight alcohol. When the reaction time exceeds 100 hours, the compound represented by the formula (1) and the produced boric acid ester are susceptible to be deteriorated. When the compound represented by the formula (1) has a (meth)acryloyl group, the reaction time is more preferably 2 to 30 hours for reasons of prevention of polymerization of the (meth)acryloyl group.

The above reaction is preferably carried out by mixing the compound represented by the formula (1) with the compound represented by the formula (2) in a predetermined proportion for 0.5 to 5 hours in an atmosphere of dry air or an inert gas. Thereafter, volatile compounds are preferably removed at a temperature of 60 to 120° C. under a reduced pressure of 6.67 kPa or below.

It is further preferred that the reduced pressure be established by gradually reducing the pressure while maintaining the reaction temperature at a constant level.

The dry air to be fed into the reaction system is not specifically limited. The dry air is, however, preferably one which is dried using a condensation-type air dryer, etc. Since the boron-containing compound represented by the formula (2) and the desired boric acid ester compound are easily hydrolyzed, it is necessary that the water content in the gas be low. For example, the dew point is −10° C. or lower.

When the boron-containing compound represented by the formula (2) used in the present invention is subjected to interesterification with the hydroxyl group-containing compound represented by the formula (1), a low molecular weight alcohol represented by the formula (3) is generated. For example, when the boron-containing compound represented by the formula (2) is trimethyl borate, the low molecular weight alcohol represented by the formula (3) is methanol. When two or more boron-containing compounds represented by the formula (2) are used, two or more low molecular weight alcohols represented by the formula (3) are generated.

The method of producing a boric acid ester compound according to the present invention comprises mixing the compound represented by the formula (1) with the compound represented by the formula (2), and reacting the mixture. After or simultaneously with the reaction, the low molecular weight alcohol represented by the formula (3) produced by the reaction and the boron-containing compound represented by the formula (2) are preferably distilled to obtain the boric acid ester compound. Distillation is generally classified into simple distillation and rectification. The term "distillation" as used in the present invention includes rectification as well as simple distillation.

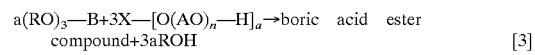

$$a(RO)_3\text{---}B+3X\text{---}[O(AO)_n\text{---}H]_a \rightarrow \text{boric acid ester compound}+3a\text{ROH} \qquad [3]$$

The production process of the present invention is to produce a high purity boric acid ester compound by using an equilibrium reaction represented by the formula [3]. The boric acid ester compound is produced with such a molar ratio that the boron atom is ⅓ mole per 1 mole of the hydroxyl group of the compound represented by the formula (1). The degree of boric acid ester production reaction can be controlled at will according to the reaction temperature, reaction time, molar ratio of the hydroxyl group to the boron atom, etc. Preferably the boric acid ester compound is produced with a reactivity of 50 to 100%, more preferably 65 to 100%.

By efficiently removing the alcohol represented by the formula (3), the reaction can proceed to increase the degree of boric acid ester production. Since the alcohol represented by the formula (3) and the boron-containing compound represented by the formula (2) have boiling points which are close to each other and tend to form a minimum azeotropic mixture, it is preferred that the distillation procedure be so selected as to efficiently remove the alcohol represented by the formula (3).

The distillation is preferably carried out at a temperature of 30 to 200° C. and a pressure ranging from an inert gas atmosphere-pressurized condition to 0.013 kPa, more preferably 0.10 to 110 kPa. When the pressure is outside the above range, there is a possibility that a special reactor is required or the control of distillation becomes difficult.

The amount of the compound represented by the formula (2) relative to the compound represented by the formula (1) is preferably such that the boron-containing compound represented by the formula (2) is used in an amount of at least ⅓ mole per 1 mole of the hydroxyl group of the compound represented by the formula (1). For the purpose of obtaining a high purity product, the boron-containing compound represented by the formula (2) is preferably used in an amount of at least 0.5 mole, more preferably at least 0.67 mole, per 1 mole of the hydroxyl group of the compound represented by the formula (1).

The amount of use of the boron-containing compound represented by the formula (2) is required to be determined in consideration of the structure, molecular weight, etc. of the compound represented by the formula (1). For example, when the compound represented by the formula (1) has a high molecular weight and when the amount of the compound represented by the formula (2) is small, there are cases in which a mixture of them becomes a solid so that the reactivity is not sufficiently high. Therefore, the amount of the boron-containing compound represented by the formula (2) is generally 80% by weight at maximum based on a total weight of the reaction liquid, although the upper limit is not specifically limited. An amount of the compound represented by the formula (2) in excess of 80% by weight requires a long distillation time and does not provide any additional merit.

The distillation can be carried out with further addition of the boron-containing compound represented by the formula (2). A method of the addition of the compound represented by the formula (2) is not specifically limited. Thus, the compound can be added in one time or continuously or intermittently with the lapse of time.

The above reaction may be carried out without using a catalyst. When an alcohol having a low reactivity, such as a tertiary alcohol, is used, sodium or potassium may be used as a catalyst for the purpose of ensuring a sufficient reaction rate. However, it is preferable not to use a catalyst in order to carry out purification with ease.

The reaction can be performed using a suitable solvent which does not participate in the reaction for the formation of a boric acid ester. As the solvent, an aprotic solvent capable of forming a minimum azeotrope with the low molecular weight alcohol represented by the formula (3) but incapable of forming a minimum azeotrope with the boron-containing compound represented by the formula (2). Specific examples of the solvent include hexane, heptane, benzene, toluene and xylene. When such a solvent is used, there is obtainable an effect that the degree of distillation of the boron-containing compound represented by the formula (2) can be reduced and that the amount of use of the boron-containing compound represented by the formula (2) can be reduced.

When a compound having a polymerizable group, such as a (meth)acryloyl group or an alkenyl group, is used as the compound represented by the formula (1), a polymerization inhibitor, such as di-t-butyl-hydroxytoluene (hereinafter referred to as BHT) and phenothiazine, can be used in an amount of 20 to 1,000 ppm to protect the polymerizable group. In the case of a polymerizable group-free compound, an anti-oxidant such as BHT can be used in an amount of 1 to 1,000 ppm for anti-oxidation.

The boric acid ester compound produced by the method of the present invention does not particularly require purification. However, the boric acid ester compound may be subjected to various purification procedures such as filtration, adsorption treatment, extraction, distillation, recrystallization, and drying, as long as such purification does not adversely affect the effect of the present invention. Since the boric acid ester compound is highly susceptible to hydrolysis, the above purification treatment is desired to be carried out under conditions which do not cause absorption of moisture or hydrolysis. For example, when the compound is treated with an adsorbing agent, it is preferable to use the agent after heating and drying.

The boric acid ester compound produced by the process of the present invention has a water content of 1,000 ppm or less, preferably 900 ppm or less, more preferably 350 ppm or less, particularly preferably 100 ppm or less, when measured by Karl Fischer titration.

The measurement of the water content by Karl Fischer titration uses methanol as a solvent for the measurement. In this measurement, not only water contained in the boric acid ester compound but also impurities such as orthoboric acid and boric anhydride contained therein in trace amounts may be measured simultaneously. When a boric acid ester compound containing a large amount of such water and impurities is used as a raw material for an electrolyte, there is an increasing possibility of causing deterioration of properties such as an increase in resistance of the solid electrolyte interface (SEI) and a reduction of potential stability. When such a boric acid ester compound is used as an electrolyte for a lithium ion secondary battery, there is a high possibility that the water and impurities contained in the boric acid ester compound react with lithium or a support salt, electrolysis is caused during charging or discharging, or gases are generated. Thus, there is caused a problem that the safety of the battery is impaired.

In the present invention, the measurement of a water content by Karl Fischer titration may be carried out by the following method. Except for the following conditions, the measurement is carried out in accordance with the Japanese Industrial Standard JIS K1557, 6.5.

The water content is measured by a volume titration method using 100 ml of dehydrated methanol for use in Karl Fischer measurement as a solvent. As a titration liquid, a reagent having a titer of 3 mg $H_2O/g$ is used. For a sample having a low water content, a greater amount (e.g. 40 g) of the sample is used than the amount (20 g) specified in JIS K1557, 6.5 for the determination of the water content. The sample is charged in a measuring vessel using a syringe. An average of two measured values for each of the samples is calculated with the number of significant digits being 2 (the third digit is treated by counting fractions of 5 and over as a unit and cutting away the rest).

The boric acid ester compound obtained by the production method according to the present invention occasionally contains a trace amount of the boron-containing compound represented by the formula (2), dependent upon the structure of the compound, method of purification, etc. When the boric acid ester compound obtained by the present invention is used as an electrolyte for electrochemical devices, it is preferred that the amount of the boron-containing compound represented by the formula (2) be reduced to 5% by weight or less, since there is a possibility that the boron-containing compound represented by the formula (2), which is volatile in nature, causes expansion or liquid leakage in the electrochemical devices.

In the production method of the present invention, there is obtained a mixture of the boron-containing compound represented by the formula (2) and the low molecular weight alcohol represented by the formula (3) as distillates. The distillates can be entirely reused. For example, the distillates can be used as a raw material for the production of a boric acid ester obtainable by reaction of an alkyl alcohol with boric acid. Further, the distillates which contain the boron-containing compound represented by the formula (2) as a main ingredient can be reused as a raw material for the production method of the present invention.

The reaction apparatus used in the production method of the present invention may be suitably selected from known apparatuses used in this field. The material of the apparatus may be suitably selected from known materials such as glass and stainless steel. The heat transfer area, heating medium, etc. may also be suitably selected in consideration of the reaction conditions. When rectification is performed, a rectifying column must be used. The separation type, number of theoretical plates, column diameter, etc. may be suitably selected so as to meet the reaction conditions. Because the boric acid ester compound is susceptible to hydrolysis, the inside of the apparatus is preferably previously dried.

The present invention is also directed to an electrolyte for an electrochemical device which has a water content of 1,000 ppm or less when measured by Karl Fischer titration and which comprises a boric acid ester compound represented by the formula (4) or a polymer thereof:

(4)

wherein Y represents a group selected from an acryloyl group, a methacryloyl group and an alkyl group having 1 to 4 carbon atoms with the proviso that at least one of Y groups is an acryloyl group or a methacryloyl group, AO is an oxyalkylene group having 2 to 4 carbon atoms, and p is 1 to 600.

The electrolyte for an electrochemical device has a water content of 1,000 ppm or less, preferably 900 ppm or less, more preferably 350 ppm or less, particularly preferably 100 ppm or less, when measured by Karl Fischer titration. The boric acid ester compound represented by the formula (4) or a polymer thereof is useful as an electrolyte for electrochemical devices. The use of such an electrolyte can provide anion capturing property and high ion conductivity. The electrolyte obtained has excellent safety and electric properties. In the formula (4), the oxyalkylene group represented by AO and having 2 to 4 carbon atoms may be the same as that defined with reference to the formula (1). As the alkyl group represented by Y and having 1 to 4 carbon atoms, there may be mentioned an alkyl group which has 1 to 4 carbon atoms and which is a residue of the compound represented by X in the formula (1) and having 1 to 6 hydroxyl group. The symbol "p" represents an average number of mols of the added oxyalkylene group having 2 to 4 carbon atoms and is 1 to 600, preferably 1 to 200, more preferably 1 to 100, for the purpose of obtaining suitable ion conductivity. When p exceeds 600, the amount of boron introduced is so small that it is difficult to provide a suitable anion capturing property when the compound is used as an electrolyte.

The above-described electrolyte for electrochemical devices may be used as an electrolyte for secondary batteries, electrical double-layer capacitors, etc. and is useful as an electrolyte for secondary batteries, particularly as an electrolyte for lithium ion secondary batteries. Further, it may be used as a secondary battery using the electrolyte for a secondary battery.

As the above-mentioned boric acid ester compound, there may be suitably used a boric acid ester compound obtainable by the method of production of a boric acid ester compound according to the present invention, namely a boric acid ester compound obtainable by using the compound represented by the formula (1) and the boron-containing compound represented by the formula (2).

Among the boric acid ester compounds according to the present invention, those compounds having a polymerizable group are used in the form in which the polymerizable groups are polymerized. The polymerization may be performed using energy such as heat, ultraviolet rays, visible light, or electron beams. Known polymerization initiators may be used if desired. The number average molecular weight of the polymer is preferably 50,000 to 10,000,000. When the number average molecular weight is less than 50,000, there is a possibility to cause a difficulty in obtaining a film having self-supporting property and flexibility from the polymer.

The boric acid ester compound according to the present invention may be used singly or as a mixture of two or more. Depending upon formulations, the use of two or more compounds as a mixture can improve mechanical properties and can improve ion conductivity when used as an electrolyte for a secondary battery.

For example, when the boric acid ester compound of the present invention is prepared by using a compound represented by the formula (1) having a polymerizable group together with a compound represented by the formula (1) having no polymerizable group, the amount of the polymerizable groups introduced and the amount of the boric acid ester groups introduced may be controlled at will. Such a boric acid ester compound is very useful from the standpoint of material design.

The boric acid ester compound according to the present invention is preferably used in an amount of 5 to 100% by weight, more preferably 10 to 100% by weight, based on an organic polymer compound for the purpose of obtaining an effect of controlling the ion transfer which contributes to the charging and discharging.

The electrolyte using the boric acid ester compound according to the present invention can achieve an improvement of ion conductivity as a consequence of an improved cation transfer efficiency by boron and can attain a resulting improvement in performance as an electrolyte for electrochemical devices. Further, because the boric acid ester compound has a substantially low water content, when the boric acid ester compound is used as an electrolyte, problems, such as occurrence of corrosion of metal parts or metal components and an increase of an internal pressure due to generation of gases as a result of electrolysis of water, are not encountered. Therefore, the boric acid ester compound is very useful.

Among the boric acid ester compounds according to the present invention, the compounds having a polymerizable group can provide excellent film stability being consistent with a high ion conductivity, because the boric acid ester groups are immobilized in the same molecules as those of the polymer matrix. Further, in the case of the boric acid ester compounds having a polymerizable group, since the boric acid ester groups are present in the same molecules as those of the polymer matrix, it is possible to use the boric acid ester compound without adding a third component in addition to an ionic compound. Thus, it is possible to simplify the steps for the production of an electrolyte film. Therefore, the polymerizable group-containing boric acid ester compound is very useful.

The electrolyte for electrochemical devices according to the present invention can be prepared by various methods and are not specifically limited. For example, the boric acid ester compound is mixed with another polymerizable organic compound, to which an ionic compound is dissolved. After casting, polymerization is performed by heating to give a polymer electrolyte film having dynamic strengths. Also, in the case of the boric acid ester compound having a polymerizable group, for example, an ionic compound is dissolved to prepare a solution. The solution is then cast by heating to polymerize thermally, thereby obtaining a polymer electrolyte film having dynamic strengths. If necessary, a film may be obtained by polymerization of a polymerizable compound by irradiation with energy rays such as ultraviolet rays, visible light, or electron beams. Further, an electrolyte film for electrochemical devices may be obtained by, for example, thoroughly kneading polymer obtained from the boric acid ester compound having a polymerizable group with an ionic compound, followed by molding.

The electrolyte for electrochemical devices comprises an organic polymer compound containing an ionic compound and the boric acid ester compound. The organic polymer compound can contain other organic polymer compounds or polymerizable compounds other than the boric acid ester, as long as the effect of the present invention is not impaired.

Examples of such other organic polymer compounds include polyacrylonitrile, acrylonitrile-methacrylic acid copolymers, acrylonitrile-methyl methacrylate copolymers, methacrylic acid-styrene copolymers, acrylonitrile-styrene copolymers, acrylonitrile-styrene-methacrylic acid copolymers, acrylonitrile-styrene-methyl methacrylate copolymers, styrene-maleic acid copolymers, and polyalkylene glycol-(meth)acrylate copolymers.

The boric acid ester compound used in the present invention may be previously mixed with any of other polymerizable compounds, in which an ionic compound is then dissolved. The mixture is then polymerized.

Examples of such other polymerizable compounds include alkyl acrylates such as methyl acrylate and butyl acrylate, alkyl methacrylate such as methyl methacrylate and butyl methacrylate, polyalkylene glycol (meth)acrylate represented by the formula (5) below, acrylonitrile, styrene, and divinylbenzene. The use of polyalkylene glycol (meth) acrylate represented by the formula (5) below is preferable.

$$Z\text{-}[O(A^2O)_m\text{--}R']_b \quad (5)$$

wherein Z represents a residue of a compound having 1 to 4 hydroxyl groups, a hydrogen atom, an acryloyl group or a methacryloyl group, $A^2O$ represents one of or a mixture of two or more of an oxyalkylene group having 2 to 4 carbon atoms, m is 0 to 150, b is 1 to 4 with the proviso that m×b is 0 to 300, and R' represents a hydrogen atom, a hydrocarbon group having 1 to 8 carbon atoms, a cyanoethyl group, an acryloyl group or a methacryloyl group, with the proviso that at least one acryloyl group or methacryloyl group is contained in the molecule.

Examples of the compound which has 1 to 4 hydroxyl groups and which is represented by Z in the formula (5) include monools such as methyl alcohol, ethyl alcohol, propyl alcohol, isopropyl alcohol, n-butyl alcohol, 2-butyl alcohol, t-butyl alcohol, n-hexyl alcohol, n-octyl alcohol, isooctyl alcohol, decyl alcohol, dodecyl alcohol, tridecyl alcohol, tetradecyl alcohol, hexadecyl alcohol, octadecyl alcohol, octadecenyl alcohol, eicosyl alcohol, tetraeicosyl alcohol, allyl alcohol, methallyl alcohol and hydroxyethyl vinyl ether; diols such as ethylene glycol, propylene glycol, butane diol, pentane diol, hexane diol and octane diol; triols such as glycerin and trimethylolpropane; and tetraols such as pentaerythritol and diglycerin.

Z is preferably a residue of methyl alcohol, ethylene glycol, propylene glycol, glycerin, trimethylolpropane, pentaerythritol or diglycerin, a hydrogen atom, an acryloyl group, or a methacryloyl group, more preferably a residue of methyl alcohol, ethylene glycol or propylene glycol, a hydrogen atom, an acryloyl group, or a methacryloyl group.

As the oxyalkylene group having 2 to 4 carbon atoms which is represented by $A^2O$ in the formula (5), there may be mentioned, for example, an oxyethylene group, an oxypropylene group, an oxybutylene group, and an oxytetramethylene group. An oxyethylene group or oxypropylene group is preferred. These groups may be used singly or in combination of two or more. When there are two or more groups, the polymerization mode may be a block type or a random type.

The compound represented by the formula (5) should contain at least one acryloyl group or at least one methacryloyl group in the molecule.

The ionic compound used in the electrolyte for electrochemical devices according to the present invention may be mixed with the organic polymer compound in any mixing proportion but is preferably used in such an amount that the oxyalkylene units contained in the boric acid ester compound are 2 to 30 moles, particularly 2 to 20 moles, in total per 1 mole of the alkali metal contained in the ionic compound for reasons of contribution to ion conductivity attributed to a lowered glass transition point of the organic polymer compound and improved ion conductivity attributed to an increase in the number of carriers. For reasons of accelerated dissociation of the ionic compound, it is preferred that the mixing ratio is such that the total oxyalkylene units be 4 to 20 moles per 1 mole of the alkali metal.

When a compound having an oxyalkylene unit other than the boric acid ester compound is blended, the oxyalkylene units thereof is also taken into account for determining the amount of the ionic compound to be blended.

The kind of the ionic compound used for forming the electrolyte for electrochemical devices according to the present invention is not specifically limited. For utilization in capacitors, the ionic compound may be, for example, a quaternary ammonium salt such as $(CH_3)_4NBF_4$ or $(CH_3CH_2)_4NBF_4$, a transition metal salt such as $AgClO_4$, a quaternary phosphonium salt such as $(CH_3)_4PBF_4$, an alkali metal salt such as $LiClO_4$, $LiAsF_6$, $LiPF_6$, $LiBF_4$, $LiCF_3SO_3$, $Li(CF_3SO_2)_2N$, $Li(C_2F_5SO_2)_2N$, $Li(CF_3SO_2)_3C$, LiI, LiSCN, NaBr, NaI, NaSCN, KI or KSCN, an organic acid such as p-toluenesulfonic acid or a salt thereof. For reasons of high output voltage and a large dissociation constant, a quaternary ammonium salt, a quaternary phosphonium salt and an alkali metal salt are preferred.

As an ionic compound used for the electrolyte for secondary batteries of the present invention, there may be mentioned alkali metal salts such as $LiClO_4$, $LiAsF_6$, $LiPF_6$, $LiBF_4$, $LiCF_3SO_3$, $Li(CF_3SO_2)_2N$, $Li(C_2F_5SO_2)_2N$, $Li(CF_3SO_2)_3C$, LiI, LiSCN, NaBr, NaI, NaSCN, KI and KSCN. Lithium salts such as $LiClO_4$, $LiAsF_6$, $LiPF_6$, $LiBF_4$, $LiCF_3SO_3$, $Li(CF_3SO_2)_2N$, $Li(C_2F_5SO_2)_2N$, $Li(CF_3SO_2)_3C$, LiI and LiSCN are preferred.

The electrolyte for secondary batteries of the present invention can contain an ion conductive or ferroelectric salt, a glass powder, etc. As the salt and glass powder, there may be mentioned $SnO_2$, $BaTiO_3$ and $LaTiO_3$.

As long as the effect of the present invention is not impaired, a mixture of a liquid electrolyte base material may be used such as of ethylene carbonate, propylene carbonate, butylene carbonate, dimethyl carbonate, diethyl carbonate, methylethyl carbonate, tetrahydrofuran, γ-butyrolactone, dimethoxyethane, 2-methyltetrahydrofuran, 1,3-dioxolane, formamide, dimethylformamide, nitromethane, methyl formate or methyl acetate.

By combining the polymer electrolyte of the present invention with previously known positive and negative pole materials, a secondary battery having excellent ion conductivity, charging and discharging cycle characteristic and safety can be obtained.

Since the method of producing a boric acid ester compound according to the present invention uses a boron-containing compound represented by the above formula (2), substantially no water is generated during the reaction for the preparation of boric acid ester, unlike in the case of the conventionally used boron-containing compound such as boron oxide or orthoboric acid. Further, since the low molecular weight alcohol generated as a result of the transesterification between the compound represented by the formula (1) and the compound represented by the formula (2) can be easily removed, it is possible to reduce the time required for the reaction. Thus, the production efficiency is excellent.

Further, by distilling the low molecular weight alcohol represented by the formula (3), which is generated as a result of the transesterification between the compound represented by the formula (1) and the compound represented by the formula (2), together with the compound of the formula (2), the boric acid ester-forming reaction can proceed with a very high reactivity. Moreover, since the boron-containing compound represented by the formula (2) which remains unconsumed during the reaction can be easily removed, it is possible to obtain a high purity boric acid ester compound.

Also, since the water content of the boric acid ester compound of the present invention is very low because no water is generated during the boric acid ester-forming reaction, the boric acid ester compound, when utilized as an electrolyte for electrochemical devices, does not induce decomposition of an ionic compound contained in the electrolyte. Further, the boric acid ester compound does not cause corrosion of metals used in the electrochemical devices and is thus excellent in electric characteristics.

Since boron oxide, orthoboric acid, metaboric acid and pyroboric acid, which are generally used for the production of boric acid ester compounds, are soluble in a polyalkylene glycol derivative, there is a possibility that they remain dissolved after the esterification. When such a boric acid ester compound is used as an electrolyte for electrochemical devices, it is likely that ion-exchange with the ionic compound contained, metal corrosion and unsuitable ion trapping will occur. With the production method according to the present invention, on the other hand, even when the boron-containing compound represented by the formula (2) remains unremoved in the boric acid ester compound, it does not react or interact with a support salt or metals. Therefore, excellent electric characteristics can be obtained.

By using the electrolyte for electrochemical devices according to the present invention, the electrochemical devices having high ion conductivity over a wide temperature range and excellent cycle characteristics, safety and stability are obtained.

Since the boric acid ester compound obtained by the production method according to the present invention has a very low water content and high purity, the remaining amount of the compounds represented by the formulas (1) and (3) is small. When such a boric acid ester compound having a low water content and a low hydroxyl group content is used in an electrolyte for a lithium ion secondary battery, it is possible to obtain a high performance electrolyte having a very small increase in internal resistance and an excellent battery using such an electrolyte.

Moreover, the method of producing a boric acid ester compound according to the present invention can produce a boric acid ester compound having any desired structure and can permit easy molecular design. Therefore, the application of such a compound for electrochemical devices exhibiting various characteristics can be easily attained.

The present invention will be further described in detail below by way of examples.

In the following descriptions, the dry air refers to a dehydrated air passed through a condensation-type air dryer, LiTFSI refers to lithium bis(trifluoromethane-sulfonate) imide, and $LiPF_6$ refers to lithium hexafluorophosphate. The added amount of LiTFSI or $LiPF_6$ which is an ionic compound for use in an electrolyte composition in each of the examples is such as to provide a Li ion concentration of 1 mole per 16 moles of the ethereal oxygen of the alkylene oxide contained in the electrolyte composition.

EXAMPLE 1

To 550 g (1.0 mole) of methoxypolyethylene glycol having a molecular weight of 550 as a starting material, 34.6 g (0.333 mole) of trimethyl borate was added and the mixture was heated to 60° C. in a nitrogen gas atmosphere with stirring. After the mixture had been maintained at 60° C. for 1 hour, the temperature was gradually increased to 120° C. through 1 hour. When the temperature of 120° C. was reached, the system was gradually evacuated and maintained at pressures of 2.67 kPa (20 mmHg) or less for 3 hours, while removing volatile matters produced as the reaction proceeded. Filtration was then carried out to give 520 g of a boric acid ester compound.

EXAMPLE 2

To 654 g (1.5 moles) of polyethylene glycol (350) monomethacrylate (BLEMMER PE-350 manufactured by NOF Corporation) as a starting material, 51.9 g (0.5 mole) of trimethyl borate was added and the mixture was heated to 60° C. in a dry air atmosphere with stirring. After the mixture had been maintained at 60° C. for 1 hour, the temperature was increased to 75° C. When the temperature of 75° C. was reached, the system was gradually evacuated and maintained at pressures of 2.67 kPa or less for 6 hours, while removing volatile matters produced as the reaction proceeded. Filtration was then carried out to give 625 g of a polymerizable boric acid ester compound.

EXAMPLE 3

To 708 g (1.5 moles) of polyethylene glycol (400) monoacrylate (BLEMMER AE-400 manufactured by NOF Corporation) as a starting material, 51.9 g (0.5 mole) of trimethyl borate was added and the mixture was heated to 60° C. in a dry air atmosphere with stirring. After the mixture had been maintained at 60° C. for 1 hour, the temperature was increased to 70° C. When the temperature of 70° C. was reached, the system was gradually evacuated and maintained at pressures of 2.67 kPa or less for 6 hours, while removing volatile matters produced as the reaction proceeded. Filtration was then carried out to give 670 g of a polymerizable boric acid ester compound.

EXAMPLE 4

To 944 g (2.0 moles) of polyethylene glycol (400) monoacrylate (BLEMER AE-400 manufactured by NOF Corporation) and 550 g (1.0 mole) of methoxypolyethylene glycol having a molecular weight of 550 as starting materials, 103.8 g (1.0 mole) of trimethyl borate was added and the mixture was heated to 60° C. in a dry air atmosphere with stirring. After the mixture had been maintained at 60° C. for 1 hour, the temperature was increased to 70° C. When the temperature of 70° C. was reached, the system was gradually evacuated and maintained at pressures of 2.67 kPa or less for 6 hours, while removing volatile matters produced as the reaction proceeded. Filtration was then carried out to give 1,430 g of a polymerizable boric acid ester compound.

COMPARATIVE EXAMPLE 1

To 550 g (1.0 mole) of methoxypolyethylene glycol having a molecular weight of 550 as a starting material, 11.6 g (0.167 mole) of boron oxide was added and the mixture was heated to 110° C. in a nitrogen gas atmosphere with stirring. When the temperature of 110° C. was reached, the system was gradually evacuated and maintained at pressures of 2.67 kPa or less for 3 hours, while removing water produced as the reaction proceeded. Filtration was then carried out to give 520 g of a boric acid ester compound.

COMPARATIVE EXAMPLE 2

To 472 g (1.0 mole) of polyethylene glycol (400) monoacrylate (BLEMMER AE-400 manufactured by NOF Corporation) as a starting material, 20.6 g (0.333 mole) of orthoboric acid was added and the mixture was heated to 70° C. in a dry air atmosphere with stirring. When the temperature of 70° C. was reached, the system was gradually evacuated and maintained at pressures of 2.67 kPa or less in a dry air stream for 6 hours, while removing water produced as the reaction proceeded. Filtration was then carried out to give 450 g of a polymerizable boric acid ester compound.

COMPARATIVE EXAMPLE 3

To 654 g (1.5 moles) of polyethylene glycol (350) monomethacrylate (BLEMMER PE-350 manufactured by NOF Corporation) as a starting material, 17.4 g (0.25 mole) of boron oxide was added and the mixture was heated to 75° C. in a dry air atmosphere with stirring. When the temperature of 75° C. was reached, the system was gradually evacuated and maintained at pressures of 2.67 kPa or less in a dry air stream for 6 hours, while removing water produced as the reaction proceeded. Filtration was then carried out to give 620 g of a polymerizable boric acid ester compound.

The boric acid ester compounds obtained in Examples 1 to 4 and Comparative Examples 1 to 3 were each measured and calculated for the water content by Karl Fischer titration in accordance with the Japanese Industrial Standard JIS K1557, 6.5 as follows.

The water content was measured by a volume titration method using 100 ml of dehydrated methanol for use in Karl Fischer measurement as a solvent. As a titration liquid, a reagent having a titer of 3 mg $H_2O$/g was used. For a sample having a low water content, a greater amount (40 g) of the sample was used than the amount (20 g) specified in JIS K1557, 6.5 for the determination of the water content. The sample was charged in a measuring vessel using a syringe. An average of two measured values for each of the samples was calculated with the number of significant digits being 2 (the third digit is treated by counting fractions of 5 and over as a unit and cutting away the rest).

EXAMPLE 5

The boric acid ester compound (5.00 g) of Example 1, 2.50 g of polyethylene glycol (600) dimethacrylate (BLEMMER PDE-600 manufactured by NOF Corporation) and 2.50 g of methoxypolyethylene glycol (4000) monomethacrylate (BLEMMER PME-4000 manufactured by NOF Corporation) were mixed together, to which 3.65 g of LiTFSI as a support salt was added and homogeneously dissolved. Then, 30 mg of azobisisobutylonitrile as a thermal polymerization initiator was added and dissolved. The resulting liquid was applied by a spin coater onto a silicon wafer. This was quiescently placed in an oven at 80° C. for 2 hours to permit thermal polymerization to proceed, thereby obtaining an ion conductive polymer composition (polymer electrolyte) having a thickness of 100 µm.

EXAMPLE 6

To 10.0 g of the polymerizable boric acid ester compound of Example 3, 3.37 g of LiTFSI as a support salt was added and homogeneously dissolved. Then, 30 mg of azobisisobutylonitrile as a thermal polymerization initiator was added and dissolved. The resulting liquid was applied by a spin coater onto a silicon wafer. This was quiescently placed in an oven at 80° C. for 2 hours to permit thermal polymerization to proceed, thereby obtaining an ion conductive polymer composition (polymer electrolyte) having a thickness of 100 µm.

EXAMPLE 7

To 10.0 g of the polymerizable boric acid ester compound of Example 4, 3.55 g of LiTFSI as a support salt was added and homogeneously dissolved. Then, 30 mg of azobisisobutylonitrile as a thermal polymerization initiator was added and dissolved. The resulting liquid was applied by a spin coater onto a silicon wafer. This was quiescently placed in an oven at 80° C. for 2 hours to permit thermal polymerization to proceed, thereby obtaining an ion conductive polymer composition (polymer electrolyte) having a thickness of 100 µm.

EXAMPLE 8

To 10.0 g of the polymerizable boric acid ester compound of Example 2, 1.71 g of $LiPF_6$ as a support salt was added and homogeneously dissolved. Then, 30 mg of azobisisobutylonitrile as a thermal polymerization initiator was added and dissolved. The resulting liquid was applied by a spin coater onto a silicon wafer. This was quiescently placed in an oven at 80° C. for 2 hours to permit thermal polymerization to proceed, thereby obtaining an ion conductive polymer composition (polymer electrolyte) having a thickness of 100 µm.

EXAMPLE 9

The polymerizable boric acid ester compound (5.00 g) of Example 2 and 5.00 g of methoxypolyethylene glycol (4000) monomethacrylate (BLEMMER PME-4000 manufactured by NOF Corporation) were mixed well with each other, to which 1.91 g of $LiPF_6$ as a support salt was added and homogeneously dissolved. Then, 30 mg of azobisisobutylonitrile as a thermal polymerization initiator was added and dissolved. The resulting liquid was applied by a spin coater onto a silicon wafer. This was quiescently placed in an oven at 80° C. for 2 hours to permit thermal polymerization to proceed, thereby obtaining an ion conductive polymer composition (polymer electrolyte) having a thickness of 100 µm.

COMPARATIVE EXAMPLE 4

To 10.0 g of the polymerizable boric acid ester compound of Comparative Example 2, 3.37 g of LiTFSI as a support salt was added and homogeneously dissolved. Then, 30 mg of azobisisobutylonitrile as a thermal polymerization initiator was added and dissolved. The resulting liquid was applied by a spin coater onto a silicon wafer. This was quiescently placed in an oven at 80° C. for 2 hours to permit thermal polymerization to proceed, thereby obtaining an ion conductive polymer composition (polymer electrolyte) having a thickness of 100 µm.

COMPARATIVE EXAMPLE 5

The boric acid ester compound (5.00 g) of Comparative Example 1, 2.50 g of polyethylene glycol (400) diacrylate (BLEMMER ADE-400 manufactured by NOF Corporation) and 2.50 g of methoxypolyethylene glycol (4000)

monomethacrylate (BLEMMER PME-4000 manufactured by NOF Corporation) were mixed together, to which 1.93 g of $LiPF_6$ as a support salt was added and homogeneously dissolved. Then, 30 mg of azobisisobutylonitrile as a thermal polymerization initiator were added and dissolved. The resulting liquid was applied by a spin coater onto a silicon wafer. This was quiescently placed in an oven at 80° C. for 2 hours to permit thermal polymerization to proceed, thereby obtaining an ion conductive polymer composition (polymer electrolyte) having a thickness of 100 µm.

COMPARATIVE EXAMPLE 6

To 10.0 g of the polymerizable boric acid ester compound of Comparative Example 2, 1.78 g of $LiPF_6$ as a support salt was added and homogeneously dissolved. Then, 30 mg of azobisisobutylonitrile as a thermal polymerization initiator was added and dissolved. The resulting liquid was applied by a spin coater onto a silicon wafer. This was quiescently placed in an oven at 80° C. for 2 hours to permit thermal polymerization to proceed, thereby obtaining an ion conductive polymer composition (polymer electrolyte) having a thickness of 100 µm.

COMPARATIVE EXAMPLE 7

The boric acid ester compound (7.50 g) of Comparative Example 3 and 2.50 g of methoxypolyethylene glycol (2000) monomethacrylate (BLEMMER PME-2000 manufactured by NOF Corporation) were mixed with each other, to which 1.80 g of $LiPF_6$ as a support salt were added and homogeneously dissolved. Then, 30 mg of azobisisobutylonitrile as a thermal polymerization initiator was added and dissolved. The resulting liquid was applied by a spin coater onto a silicon wafer. This was quiescently placed in an oven at 80° C. for 2 hours to permit thermal polymerization to proceed, thereby obtaining an ion conductive polymer composition (polymer electrolyte) having a thickness of 100 µm.

The polymer electrolytes obtained in Examples 5 to 9 and Comparative Examples 4 to 7 were evaluated for the film formability and stability.

The film formability of all the polymer electrolytes was found to be satisfactory for use as an electrolyte for electrochemical devices.

The stability of the polymer electrolytes was evaluated by the following method.

Each of the polymer electrolyte films was sandwiched between two sheets of metal lithium foils each having a thickness of 50 µm. The assembly was placed in a thermostatic bath at 50° C. in an argon atmosphere. After the passage of one day and seven days from the placement, the appearance of each electrolyte film and the condition of the surface of the lithium foils in contact with the electrolyte film were observed.

○: No changes at all in the appearance of the electrolyte film or the contacting surface of the metal lithium foils Δ: Coloring occurred in the appearance of the electrolyte film and partial corrosion of the contacting surface of the metal lithium foils ×: Coloring occurred in the appearance of the electrolyte film and significant corrosion of the metal lithium foils The polymer electrolytes obtained in Examples 5, 7 and 9 and Comparative Examples 5 and 6 were evaluated for ion conductivity. The measurement of ion conductivity was carried out by the following method.

The above assembly obtained by sandwiching each film between two sheets of metal lithium foils was sandwiched between stainless steel electrodes to form a non-blocking electrode. AC complex impedances at various temperatures were measured in an argon atmosphere while varying the temperature. The ion conductivity was determined from the diameter of the semicircle of bulk resistance component in the thus obtained plot (Cole-Cole plot) on the complex plane.

EXAMPLE 10

75 parts by weight of cobalt(⅙)-substituted lithium manganate powder having a Spinel structure and represented by the compositional formula of $LiCo_{1/6}Mn_{11/6}O_4$ as a positive pole active material, 5 parts by weight of polyvinylidene fluoride powder as a binder polymer and 20 parts by weight of acetylene black powder as a conductive material were kneaded well and the mixture was applied by a hot press method onto a copper foil to obtain a positive pole material having a thickness of 100 µm and a diameter of 10 mm. A metal lithium foil having a thickness of about 80 µm and a diameter of 10 mm and serving as an alkali metal ion occlusion material was used as a negative pole material. The polymer electrolyte of Example 6 was stamped into a disc having a diameter of 10 mm, which was sandwiched between the above positive pole and negative pole materials. This was further sandwiched between stainless steel electrodes to obtain a secondary battery.

The thus obtained secondary battery was subjected to 300-cycle charging and discharging treatment, with each cycle including charging to 4.15 V with a current density of 200 mA/m² at 50° C. or 80° C. and discharging to 3.50 V with a current density of 220 mA/m². The discharge capacitances per 1 kg of the positive pole at 100th and 300th cycles were measured for each battery and evaluated in terms of percentages based on the initial capacitance (1st cycle).

◎: Discharge capacitance is 70% or more of the initial capacitance

○: Discharge capacitance is less than 70% but not less than 40% of the initial capacitance Δ: Discharge capacitance is less than 40% of the initial capacitance ×: Unable to evaluate because of occurrence of internal short-circuit, deterioration of pole materials, or insufficient conductivity

EXAMPLE 11

A secondary battery was constructed using the same composition as that of Example 10, except that the polymer electrolyte of Example 8 was used. The charging and discharging cycle test was conducted in the same conditions as those in Example 10.

COMPARATIVE EXAMPLE 8

A secondary battery was constructed using the same composition as that of Example 10, except that the polymer electrolyte of Comparative Example 4 was used. The charging and discharging cycle test was conducted in the same conditions as those in Example 10.

COMPARATIVE EXAMPLE 9

A secondary battery was constructed using the same composition as that of Example 10, except that the polymer electrolyte of Comparative Example 7 was used. The charging and discharging cycle test was conducted in the same conditions as those in Example 10.

The compounds represented by the formula (1), the boron-containing compounds, the time which was required for the reaction and for which the reduced pressure was maintained, and the water content employed for producing the boric acid ester compounds in Examples 1 to 4 and Comparative Examples 1 to 3 are shown in Table 1. Further, the composition of the electrolytes, kinds of the ionic compounds and stability evaluation results of the electrolyte films in Examples and Comparative Examples are shown in Table 2. The evaluation results for ion conductivity at 25° C. and 80° C. are shown in Table 3. The evaluation results of the charging and discharging tests at 50° C. and 80° C. are shown in Table 4.

In Tables 1 and 2, M represents a methacryloyl group, A represents an acryloyl group and EO represents an oxyethylene group.

TABLE 3

| | Conductivity (S/m) | |
|---|---|---|
| No. | 25° C. | 80° C. |
| Example 5 | $5.75 \times 10^{-4}$ | $2.06 \times 10^{-2}$ |
| Example 7 | $3.37 \times 10^{-4}$ | $1.55 \times 10^{-2}$ |
| Example 9 | $1.06 \times 10^{-4}$ | $1.03 \times 10^{-1}$ |
| Comparative Example 5 | $2.10 \times 10^{-7}$ | $5.40 \times 10^{-4}$ |
| Comparative Example 6 | $1.23 \times 10^{-6}$ | $3.93 \times 10^{-4}$ |

TABLE 1

| | Compound of formula (1) | Mole ratio of compound of formula (1) | Boron-containing compound used for reaction | Water content (ppm) | Time of reduced pressure required for reaction (hr) |
|---|---|---|---|---|---|
| Example 1 | $CH_3O\text{-}(EO)_{11.8}\text{-}H$ | — | Trimethyl borate | 42 | 3.0 |
| Example 2 | $MO\text{-}(EO)_{8.0}\text{-}H$ | — | Trimethyl borate | 120 | 6.0 |
| Example 3 | $AO\text{-}(EO)_{9.1}\text{-}H$ | — | Trimethyl borate | 320 | 6.0 |
| Example 4 | $AO\text{-}(EO)_{9.1}\text{-}H/CH_3O\text{-}(EO)_{11.8}\text{-}H$ | 2/1 | Trimethyl borate | 220 | 6.0 |
| Comparative Example 1 | $CH_3O\text{-}(EO)_{11.8}\text{-}H$ | — | Boric anhydride | 1,400 | 3.0 |
| Comparative Example 2 | $AO\text{-}(EO)_{9.1}\text{-}H$ | — | Orthoboric acid | 5,200 | 6.0 |
| Comparative Example 3 | $MO\text{-}(EO)_{8.0}\text{-}H$ | — | Boric anhydride | 3,700 | 6.0 |

TABLE 2

| No. | Boric acid ester compound | Other polymerizable compound | Ratio of boric acid ester compound to other polymerizable compound (weight ratio) | Ionic compound | Results of stability tests 1 day | 7 days |
|---|---|---|---|---|---|---|
| Example 5 | Example 1 | $MO\text{-}(EO)_{13.6}\text{-}M/MO\text{-}(EO)_{90.9}\text{-}CH_3$ | = 50/25/25 | LiTFSI | ○ | ○ |
| Example 6 | Example 3 | none | = 100/0 | ↑ | ○ | ○ |
| Example 7 | Example 4 | none | = 100/0 | ↑ | ○ | ○ |
| Example 8 | Example 2 | none | = 100/0 | $LiPF_6$ | ○ | ○ |
| Example 9 | Example 2 | $MO\text{-}(EO)_{90.9}\text{-}CH_3$ | = 50/50 | ↑ | ○ | ○ |
| Comparative Example 4 | Comparative Example 2 | none | = 100/0 | LiTFSI | Δ | X |
| Comparative Example 5 | Comparative Example 1 | $AO\text{-}(EO)_{9.1}\text{-}A/MO\text{-}(EO)_{90.9}\text{-}CH_3$ | = 50/25/25 | $LiPF_6$ | Δ | X |
| Comparative Example 6 | Comparative Example 2 | none | = 100/0 | ↑ | X | X |
| Comparative Example 7 | Comparative Example 3 | $MO\text{-}(EO)_{45.5}\text{-}CH_3$ | = 75/25 | ↑ | X | X |

TABLE 4

| No. | Electrolyte | Testing temperature (° C.) | Initial capacitance (Ah/kg) | Discharge capacitance at 100th cycle (Ah/kg) | Evaluation | Discharge capacitance at 300th cycle (Ah/kg) | Evaluation |
|---|---|---|---|---|---|---|---|
| Example 10 | Example 6 | 50 | 112 | 93 | ◎ | 85 | ◎ |
|  |  | 80 | 119 | 98 | ◎ | 90 | ◎ |
| Example 11 | Example 8 | 50 | 115 | 93 | ◎ | 86 | ◎ |
|  |  | 80 | 123 | 100 | ◎ | 91 | ◎ |
| Comparative Example 8 | Comparative Example 4 | 50 | 84 | — | X | — | X |
|  |  | 80 | 96 | — | X | — | X |
| Comparative Example 9 | Comparative Example 7 | 50 | X | — | X | — | X |
|  |  | 80 | X | — | X | — | X |

It was confirmed that, whereas the boric acid ester compounds obtained in Comparative Examples 1 to 3 had high water contents, the boric acid ester compounds obtained in Examples 1 to 4 had very low water contents in spite of the fact that the reaction temperature and time were the same.

The electrolytes for electrochemical devices using the boric acid ester compounds obtained in the Examples showed no corrosion of the alkali metal and had excellent stability and high ion conductivity. Further, they were confirmed as showing excellent cycle characteristics as electrolytes for secondary batteries.

EXAMPLE 12

As starting materials, 1,110 g (3.0 moles) of polyethylene glycol (6.8 moles) monoacrylate (BLEMMER AE-300 manufactured by NOF Corporation) having an average molecular weight of 370 and 934.2 g (9.0 moles) of trimethyl borate were charged, to which 0.33 g of BHT was added. The mixture was heated to 70° C. at atmospheric pressure while blowing dry air with stirring. After the mixture had been maintained at 70° C. for 1 hour, the system was gradually evacuated to 2.67 kPa at 70° C. over 8 hours, while removing methanol produced by the reaction as a by-product and trimethyl borate by distillation. The reaction mixture was then maintained at 2.67 kPa at 70° C. for 3 hours for drying, thereby obtaining 1,100 g of the desired boric acid ester compound.

EXAMPLE 13

As starting materials, 870 g (3.0 moles) of polyethylene glycol (4.6 moles) monomethacrylate (BLEMMER PE-200 manufactured by NOF Corporation) having an average molecular weight of 290, 330 g (1.5 moles) of nonylphenol and 778.5 g (7.5 moles) of trimethyl borate were charged, to which 0.33 g of BHT was added. The mixture was heated to 70° C. at atmospheric pressure while blowing dry air with stirring. After the mixture had been maintained at 70° C. for 1 hour, the system was gradually evacuated to 2.67 kPa at 70° C. over 8 hours, while removing methanol produced by the reaction as a by-product and trimethyl borate by distillation. The reaction mixture was then maintained at 2.67 kPa at 70° C. for 3 hours for drying, thereby obtaining 1,100 g of the desired boric acid ester compound.

EXAMPLE 14

As starting materials, 1,500 g (1.5 moles) of methoxy-polyoxyethylene(16.5 moles)-propylene glycol (4.2 moles) random copolymer having an average molecular weight of 1,000 and 470 g (2.5 moles) of triisopropyl borate were charged. The mixture was heated to 130° C. in a nitrogen gas atmosphere with stirring. After the mixture had been maintained at 130° C. for 1 hour, the system was gradually evacuated to 2.67 kPa at 130° C. over 8 hours, while removing isopropanol produced by the reaction as a by-product and triisopropyl borate by distillation. The reaction mixture was then maintained at 2.67 kPa at 130° C. for 3 hours for drying, thereby obtaining 1,400 g of the desired boric acid ester compound.

EXAMPLE 15

As starting materials, 185 g (0.5 mole) of polyethylene glycol (6.8 moles) monoacrylate (BLEMMER AE-300 manufactured by NOF Corporation) having an average molecular weight of 370, 1,000 g (1.0 mole) of methoxy-polyoxyethylene (16.5 moles)-polyoxypropylene(4.2 moles) random copolymer having an average molecular weight of 1,000, 103.8 g (1.0 mole) of trimethyl borate and 0.59 g of BHT were charged. The mixture was heated to 60° C. while blowing dry air with stirring. After the mixture had been maintained at 60° C. for 1 hour, the system was gradually evacuated to 2.67 kPa at 60° C. over 4 hours, while removing methanol produced by the reaction as a by-product and trimethyl borate by distillation. The pressure was then returned to atmospheric pressure, and 103.8 g (1.0 mole) of trimethyl borate were added to the reaction mixture. This was then gradually evacuated to 2.67 kPa at 60° C. over 4 hours, while removing methanol produced by the reaction as a by-product and trimethyl borate by distillation. The reaction mixture was then maintained at 2.67 kPa at 60° C. for 2 hours for drying, thereby obtaining 1,100 g of the desired boric acid ester compound.

EXAMPLE 16

In a 3 liter four-necked flask equipped with a distillation column, 928 g (3.2 moles) of polyethylene glycol (4.6 moles) monomethacrylate (BLEMMER PE-200 manufactured by NOF Corporation) having an average molecular weight of 290, 320 g (0.8 mole) of polyethylene glycol (8.7 mole) having an average molecular weight of 400, 1246 g (12.0 moles) of trimethyl borate and 0.62 g of BHT were charged. The mixture was heated to a temperature at which refluxing occurred (50 to 65° C.) at 68 kPa while blowing dry air. After the mixture had been fully refluxed for 30 minutes, a distillate was removed from the top of the column at a reflux ratio of 10 for 5 hours. As the distillation proceeded, the temperature in the flask and the temperature at the top of the column increased. Thus, when the column top temperature of 60° C. was reached, the distillation was carried out for 3 hours at a reflux ratio of 20.

Thereafter, the trimethyl borate contained in the reaction liquid in the flask was distilled to a temperature within the flask of 60° C. or less and to a pressure of 2.67 kPa. Then the reaction liquid was maintained at 60° C. and at 2.67 kPa for 2 hours for drying, thereby obtaining 1,150 g of the desired boric acid ester compound.

COMPARATIVE EXAMPLE 10

To 2,220 g (6.0 moles) of polyethylene glycol (6.8 moles) monoacrylate (BLEMMER AE-300 manufactured by NOF Corporation) having an average molecular weight of 370 as a starting material, 69.6 g (1.0 mole) of boric oxide and 0.67 g of BHT were added. The mixture was heated to 80° C. while blowing dry air with stirring. When a temperature of 80° C. was reached, the system was gradually evacuated and maintained at 2.67 kPa or less for 3 hours, while removing water produced as the reaction proceeded. The filtration of the reaction mixture gave 2,100 g of the desired boric acid ester compound.

COMPARATIVE EXAMPLE 11

To 1,480 g (4.0 moles) of polyethylene glycol (6.8 moles) monoacrylate (BLEMMER AE-300 manufactured by NOF Corporation) having an average molecular weight of 370 and 2,000 g (2.0 moles) of methoxypolyoxyethylene (16.5 moles)-polyoxypropylene(4.2 moles) random copolymer having an average molecular weight of 1,000 as starting materials, 55.7 g (0.8 mole) of boric oxide were added. The mixture was heated to 80° C. while blowing dry air with stirring. When a temperature of 80° C. was reached, the system was gradually evacuated and maintained at 2.67 kPa or less for 3 hours, while removing water produced as the reaction proceeded. The filtration of the reaction mixture gave 3,400 g of the desired boric acid ester compound.

COMPARATIVE EXAMPLE 12

To 580 g (2.0 moles) of polyethylene glycol (4.6 moles) monomethacrylate (BLEMMER PE-200 manufactured by NOF Corporation) having an average molecular weight of 290 and 200 g (0.5 mole) of polyethylene glycol (8.7 mole) having an average molecular weight of 400 as starting materials, 61.8 g (1.0 mole) of boric acid and 0.23 g of BHT were added. The mixture was heated to 80° C. while blowing dry air with stirring. When a temperature of 80° C. was reached, the system was gradually evacuated and maintained at 2.67 kPa or less for 3 hours, while removing water produced as the reaction proceeded. The filtration of the reaction mixture gave 520 g of the desired boric acid ester compound.

[Evaluation of Boric Acid Ester Compounds]

Method of Measuring Water Content:

Evaluation was carried out in the same manner as described previously.

The boric acid ester compounds obtained in Examples 12 to 16 and Comparative Examples 10 to 12 were each measured for the boron concentration according to the following method.

In this case, theoretical boron concentration is defined as a concentration of boron on an assumption that only the compound represented by the formula (1) is completely esterified and no other compounds are contained. The purity of each compound is shown as (boron concentration)/(theoretical boron concentration).

Method of Measuring Boron Concentration:

A quantity (1 to 50 g) of the obtained boric acid ester compound corresponding to an inferred boron concentration is weighed. This is added into 100 ml of a glycerin/ion exchanged water (50/50 by volume) mixed solution. The mixture is stirred at room temperature for 5 minutes, to which 2 to 3 drops of a 1% phenolphthalein solution were added. Titration was then carried out using $1/10$ N aqueous sodium hydroxide solution until discoloration of phenolphthalein (from colorless to purple) is observed. The boron concentration is calculated from the following equation (7):

$$\text{Boron concentration (mol/kg)} = (a-b) \times f/w \quad (7)$$

a: amount of $1/10$ N aqueous sodium hydroxide solution used in titration (ml)

b: amount of $1/10$ N aqueous sodium hydroxide solution used in blank titration (ml)

w: amount of sample (g)

f: factor of $1/10$ N aqueous sodium hydroxide solution

TABLE 5

| | Compound of formula (1) | Mole ratio of compound of formula (1) | Hydroxyl value (mgKOH/g) | Compound of formula (2) | Water content (ppm) | Boron concentration (mol/kg) | Purity (%) |
|---|---|---|---|---|---|---|---|
| Example 12 | AO-(EO)$_{6.8}$-H | — | 152 | Trimethyl borate | 45 | 0.886 | 99 |
| Example 13 | MO-(EO)$_{4.6}$-H: C$_9$H$_{19}$-Ph-OH | 2:1 | 210 | Trimethyl borate | 29 | 1.213 | 98 |
| Example 14 | CH$_3$O-[(EO)$_{16.5}$/PO$_{4.2}$]-H | — | 56 | Triisopropyl borate | 54 | 0.336 | 101 |
| Example 15 | AO-(EO)$_{6.8}$-H: CH$_3$O-[(EO)$_{16.5}$/PO$_{4.2}$]-H | 1:2 | 71 | Trimethyl borate | 87 | 0.416 | 99 |

TABLE 5-continued

| | Compound of formula (1) | Mole ratio of compound of formula (1) | Hydroxyl value (mgKOH/g) | Compound of formula (2) | Water content (ppm) | Boron concentration (mol/kg) | Purity (%) |
|---|---|---|---|---|---|---|---|
| Example 16 | MO-$(EO)_{4.6}$-H: HO-$(EO)_{8.7}$-H | 4:1 | 216 | Trimethyl borate | 51 | 1.269 | 100 |
| Comparative Example 10 | AO-$(EO)_{6.8}$-H | — | 152 | (Boric anhydride) stoichiometric reaction | 2400 | 0.850 | 95 |
| Comparative Example 11 | AO-$(EO)_{6.8}$-H: $CH_3O$-$[(EO)_{16.5}/PO_{4.2}]$-H | 1:2 | 71 | (Boric anhydride) excessive OH | 960 | 0.332 | 79 |
| Comparative Example 12 | MO-$(EO)_{4.6}$-H: HO-$(EO)_{8.7}$-H | 4:1 | 216 | (Orthoboric acid) stoichiometric reaction | 3400 | 1.193 | 94 |

In Table 5, EO represents an oxyethylene group, PO represents an oxypropylene group, M represents a methacryloyl group, A represents an acryloyl group, Ph represents a phenylene group and [/] indicates a random copolymer.

[Evaluation as Electrolytes for Lithium Ion Secondary Batteries]

[Polymer Electrolyte]

To each of the boric acid ester compounds obtained in Examples 12 and 16 and Comparative Examples 10 and 12, LiFTSI was added in an amount of 20% by weight and thoroughly mixed to obtain a homogeneous mixture. Then, AIBN (azoisobutylonitrile) was added to the mixture in an amount of 0.1% by weight. This was subjected to a thermal polymerization at 80° C. The polymer was then molded into a disc having a thickness of 1.0 mm and a diameter of 14 mm, thereby obtaining a polymer electrolyte.

[Positive Pole]

A positive pole active material represented by $LiNi_{0.9}Co_{0.1}O_2$ was pulverized in a mortar to obtain positive pole active material powder. The powder was mixed with acetylene black as a conductive agent and polyvinylidene fluoride as a binding agent in a mixing ratio of 43:3:2 to obtain a positive pole formulation. This was subjected to a press molding into a disc having a diameter of 14 mm, followed by thermal treatment to obtain a positive pole.

[Negative Pole]

A metal lithium having a predetermined thickness was stamped into a disc having a diameter of 14 mm to obtain a negative pole.

Preparation of Lithium Ion Secondary Battery and Evaluation Thereof:

The above polymer electrolytes, positive pole and negative pole were assembled to obtain lithium ion secondary batteries of Examples 17 and 18 and Comparative Examples 13 and 14. Each of the thus obtained secondary batteries was sealed in an argon atmosphere and measured for initial internal resistance at 60° C. Then, each battery was stored at 60° C. for 100 hours and measured for the internal resistance again.

The evaluation results are shown in Table 6.

TABLE 6

| | Boric acid ester compound used for polymer electrolyte | Internal resistance (Ω) | | |
|---|---|---|---|---|
| | | Initial value | Value after storage | Increment |
| Example 17 | Example 12 | 6850 | 7320 | 470 |
| Example 18 | Example 16 | 10450 | 11070 | 620 |
| Comparative Example 13 | Comparative Example 10 | 7280 | 9490 | 2210 |
| Comparative Example 14 | Comparative Example 12 | 12350 | 15550 | 3200 |

Comparative Examples 10 to 12 merely gave boric acid ester compounds having a low water content or low purity. On the other hand, with Examples 12 to 16, it is possible to obtain boric acid ester compounds having a low water content and a high reactivity or having a high purity.

When the boric acid ester compounds obtained in the production method according to the present invention are used as electrolytes for lithium ion secondary batteries, it is possible to obtain batteries which are small in an internal resistance increase during storage. Thus, high performance electrolytes and secondary batteries could be obtained.

INDUSTRIAL APPLICABILITY

Since the boric acid ester compound obtained by the production method according to the present invention has a very low water content and high purity, the remaining amount of the compounds represented by the formulas (1) and (3) is small. When such a boric acid ester compound having a low water content and a low hydroxyl group content is used in an electrolyte for a lithium ion secondary battery, it is possible to obtain a high performance electrolyte having a very small internal resistance and an excellent battery using such an electrolyte.

Moreover, the method of producing a boric acid ester compound according to the present invention can produce a boric acid ester compound having any desired structure and can permit easy molecular design. Therefore, the application of such a compound for electrochemical devices exhibiting various characteristics can be easily attained.

What is claimed is:

1. A process for producing a boric acid ester compound which comprises esterifying a compound represented by the formula (1):

$$X-[O(AO)_n-H]_a \quad (1)$$

wherein X represents a group selected from a residue of a compound having 1 to 8 hydroxyl groups, an acryloyl group and a methacryloyl group, AO represents an oxyalkylene group having 2 to 4 carbon atoms, n is 1 to 600, a is 1 to 6, and n×a is 1 to 600 with a boron-containing compound represented by the formula (2):

$$(RO)_3-B \quad (2)$$

wherein R represents an alkyl group having 1 to 4 carbon atoms, while distilling the boron-containing compound represented by the formula (2) and an alcohol represented by the formula (3) and produced by said reaction:

$$ROH \quad (3)$$

wherein R represents an alkyl group having 1 to 4 carbon atoms.

2. The process for producing a boric acid ester compound as recited in claim 1, wherein the compound represented by the formula (1) has an average molecular weight of 110 or more.

3. The process for producing a boric acid ester compound as recited in claim 1, wherein the boron-containing compound represented by the formula (2) is used in an amount of ⅓ mole or more per 1 mole of the hydroxyl group of the compound represented by the formula (1).

4. The process for producing a boric acid ester compound as recited in claim 1, wherein the boric acid ester compound has a water content of 1,000 ppm or less when measured by Karl Fischer titration.

5. An electrolyte for an electrochemical device, which comprises a boric acid ester compound obtained by the process recited in claim 1 or a polymer thereof.

6. A secondary battery using the electrolyte for an electrochemical device as recited in claim 5.

7. An electrolyte for an electrochemical device, which has a water content of 1,000 ppm or less when measured by Karl Fischer titration and which comprises a boric acid ester compound represented by the formula (4) or a polymer thereof:

$$B-[O(AO)_p-Y]_3 \quad (4)$$

wherein Y represents a group selected from an acryloyl group, a methacryloyl group and an alkyl group having 1 to 4 carbon atoms with the proviso that at least one of Y groups is an acryloyl group or a methacryloyl group, AO is an oxyalkylene group having 2 to 4 carbon atoms, and p is 1 to 600.

8. An electrolyte for an electrochemical device, which comprises a boric acid ester compound obtainable by the process recited in claim 2 or a polymer thereof.

9. A secondary battery using the electrolyte for an electrochemical device as recited in claim 8.

10. An electrolyte for an electrochemical device, which comprises a boric acid ester compound obtainable by the process recited in claim 3 or a polymer thereof.

11. A secondary battery using the electrolyte for an electrochemical device as recited in claim 10.

12. An electrolyte for an electrochemical device, which comprises a boric acid ester compound obtainable by the process recited in claim 4 or a polymer thereof.

13. A secondary battery using the electrolyte for an electrochemical device as recited in claim 12.

14. The process for producing a boric acid ester compound as recited in claim 1, wherein water content of said compound represented by the formula (1) is 0.5% by weight or less.

15. The process for producing a boric acid ester compound as recited in claim 1, including a further step, prior to said esterifying, of reducing water content of said compound represented by the formula (1).

* * * * *